United States Patent
Costa Perez et al.

(10) Patent No.: US 7,252,965 B2
(45) Date of Patent: Aug. 7, 2007

(54) **METHOD OF PRODUCTION OF β-CAROTENE BY FERMENTATION IN MIXED CULTURE USING (+) AND (−) STRAINS OF *BLAKESLEA TRISPORA***

(75) Inventors: Javier Costa Perez, León (ES); Ana Teresa Marcos Rodríguez, León (ES); Juan Luis De La Fuente Moreno, León (ES); Marta Rodríguez Saiz, León (ES); Bruno Diez Garcia, León (ES); Enrique Peiro Cezon, León (ES); Walter Cabri, León (ES); José Luis Barredo Fuente, León (ES)

(73) Assignee: Antibioticos, S.A.U., Leon (ES)

( * ) Notice: Subject to any disclaimer, the term of this patent is extended or adjusted under 35 U.S.C. 154(b) by 461 days.

(21) Appl. No.: 10/469,190

(22) PCT Filed: Jan. 23, 2003

(86) PCT No.: PCT/ES03/00047
§ 371 (c)(1), (2), (4) Date: Jan. 21, 2004

(87) PCT Pub. No.: WO03/064673
PCT Pub. Date: Aug. 7, 2003

(65) Prior Publication Data
US 2004/0152154 A1  Aug. 5, 2004

(30) Foreign Application Priority Data
Jan. 29, 2002  (ES) ................. 200200202

(51) Int. Cl.
*C12P 23/00* (2006.01)
(52) U.S. Cl. .................................... 435/67
(58) Field of Classification Search ............ 435/67
See application file for complete search history.

(56) References Cited

U.S. PATENT DOCUMENTS

| | | | | |
|---|---|---|---|---|
| 5,328,845 A | * | 7/1994 | Finkelstein et al. | 435/254.1 |
| 5,422,247 A | * | 6/1995 | Finkelstein et al. | 435/67 |
| 5,643,719 A | * | 7/1997 | Cerda-Olmedo et al. | 435/6 |
| 2004/0067550 A1 | * | 4/2004 | Costa Perez et al. | 435/67 |

* cited by examiner

*Primary Examiner*—Herbert J. Lilling
(74) *Attorney, Agent, or Firm*—Ladas & Parry LLP (57) ABSTRACT

The invention consists of fermenting selected strains of *Blakeslea trispora* in conditions such that β-carotene is produced in the form of stabilized preparations with residual contents of other carotenoids (γ-carotene and β-zeacarotene). The fermentation conditions chosen include the programmed addition of oxygen and/or β-ionone during fermentation, and control of the age of the vegetative growth phases of the strains employed. The β-carotene obtained can be used in the pharmaceutical and food sectors.

16 Claims, 3 Drawing Sheets

METHOD OF PRODUCTION OF β-CAROTENE BY FERMENTATION IN MIXED CULTURE USING (+) AND (−) STRAINS OF *BLAKESLEA TRISPORA*

FIELD OF THE INVENTION

This application is a 371 of PCT/ES03/00047 filed Jan. 23, 2003 which claims benefit to foreign application Spain P 200200202 filed Jan. 29, 2002.

The present invention describes methods of selecting (+) and (−) strains of *Blakeslea trispora* that are overproducers of β-carotene and a new method of fermentation of the said strains that makes it possible to obtain stabilized preparations of β-carotene for direct application in the foodstuffs and pharmaceuticals fields.

DESCRIPTION OF RELATED ART

The carotenoids are pigments of isoprenoid nature that are synthesized by certain bacteria, fungi and photosynthetic organisms. They can be divided into two types: (i) pure hydrocarbons called carotenes, including compounds such as β-carotene, α-carotene, γ-carotene or lycopene and (ii) molecules called xanthophylls, which contain oxygen in various forms (hydroxyl groups, epoxy groups, etc.), including astaxanthin, zeaxanthin, capsanthin, cantaxanthin, lutein, etc. All these compounds play an important role in the human diet, as antioxidants (prevention of cancer and other diseases) and as precursors of vitamin A. Owing to their beneficial effects on health and their attractive colors, the carotenoids are of considerable commercial importance as colorants and food additives [Ninet L. and Renaut J. (1979) In: Peppler H J., Perlman D. (eds). Microbial Technology, $2^{nd}$ Edition, Vol. 1, Academic Press, NY, pp. 529-544].

β-Carotene is a carotenoid whose chemical synthesis has been known since 1956. It has a molecular weight of 536.9 and a molecule ($C_{40}H_{56}$) with eleven conjugated double bonds. Its color is reddish violet in the crystalline state, yellowish orange in oily solution and orange in aqueous dispersion. Synthetic β-carotene has the all-trans isomeric configuration, whereas β-carotene from various natural sources has a variety of forms: all-trans, mono-cis, di-cis and poly-cis.

The production of carotenoids by microbial biosynthesis is a classic example of competition between chemical and biological processes. Advantages of the biotechnological processes include, among others, the possibility of obtaining, in a simple way, the carotenoids of more complex structure, as well as the conformational isomers that only occur naturally. The industrial biotechnological processes for production of β-carotene, competing with chemical synthesis, are based on the use of the alga *Dunaliella salina* and the fungus *B. trispora*. The production process with *B. trispora* involves carrying out a mixed fermentation of the (+) and (−) strains to achieve a maximum yield of β-carotene. The increase in yield of carotenoids in mixed cultures is related to the production of a family of acid compounds called factor β or trisporic acids [WO 00/77234, Caglioti L. et al. (1966) Tetrahedron Supplement 7: 175-187]. β-Carotene is produced by both the (+) strain and the (−) strain, being metabolized by both to retinal and subsequently to 4-dihydrotrisporol. The (+) strain utilizes the 4-dihydrotrisporol as substrate for forming dihydro-trisporic acid and its methyl ester (methyl-4-dihydro-trisporate). For its part, the (−) strain metabolizes the 4-dihydrotrisporol to trisporol. Finally, the methyl-4-dihydrotrisporate is converted to trisporic acid by the (−) strain and the trisporol is converted to trisporic acid by the (+) strain. This description of the biosynthesis of the trisporic acids is a simplification, since during the process many co-metabolites are generated, some of which are common to both strains (+) and (−), but others are specific to one of them. The relative quantities of these co-metabolites vary depending on the strains.

The biosynthetic pathway of β-carotene (Scheme 1) has been described in fungi that are related phylogenetically to *B. trispora* such as *Phycomyces blakesleeanus* and *Mucor circinelloides* [Arrach N. et al. (2001) Proceedings of the National Academy of Sciences USA 98: 1687-1692; Velayos A. et al. (2000) European Journal of Biochemistry 267: 5509-5519]. At least three enzymes are necessary for the said biosynthesis: (i) phytoene synthase, which joins together two molecules of geranylgeranyl pyrophosphate to form phytoene, (ii) phytoene dehydrogenase, which introduces four double bonds into the phytoene molecule to synthesize lycopene, and (iii) lycopene cyclase, which, using lycopene as substrate, forms the rings located at the two ends of the β-carotene molecule. It was concluded on the basis of analysis of mutants of *B. trispora* that the biosynthetic pathway of β-carotene in this fungus is similar to that described for *P. blakesleeanus* [Metha B. J. and Cerdá-Olmedo E. (1995) Applied Microbiology and Biotechnology 42: 836-838]. In the case of *P. blakesleeanus*, the yellow color of its mycelium can be altered by mutation, giving rise to strains with mycelium colored red, white or various shades of yellow. The red mutants accumulate lycopene, whereas the white ones lack production of carotenoids or accumulate phytoene.

Scheme 1

Mevalonate

One of the systems used in industrial microbiology for selecting strains is based on flow cytometry. With this technique it is possible to select subpopulations of mutants from a heterogeneous population. To achieve this, non-destructive methods are used, such as measurement of fluorescence and of the scattering of light. Isolation of the mutants is effected by means of an accessory connected to the cytometer ("Sort") that permits cell sorting and separation. Selection of subpopulations is based on measurement of particular parameters that are related directly or indirectly to the yield. Flow cytometry is particularly useful for biological samples whose product of interest is autofluorescent. Although β-carotene is not actually a fluorescent molecule, when it is excited with an argon laser at a wavelength of 488 nm, as it returns from the excited state to its base state the energy loss gives rise to a process of radiation transfer which is detected at a wavelength above 600 nm. This property permits the direct selection of the mutants of interest.

The production of β-carotene by fermentation of B. trispora is described in patents U.S. Pat. No. 3,522,146, SU 1592327, RU 2053301 and U.S. Pat. No. 5,422,247. U.S. Pat. No. 5,422,247 claims the production of 3.5 to 7 g/l of β-carotene using selected strains of B. trispora in specific fermentation conditions. The present patent describes new methods of selection of strains and improved conditions of fermentation that make it possible to produce 9 g/l of β-carotene.

SUMMARY OF THE INVENTION

The present invention describes a series of methods for obtaining high yields of β-carotene with the fungus *B. trispora*. The invention consists of (i) the design of methods for the production and selection of mutants of *B. trispora* that are overproducers of β-carotene and (ii) the development of improved conditions of fermentation. *B. trispora* is a fungus that is of considerable industrial importance for the biotechnological production of β-carotene. In fact, this process proves to be competitive with the synthetic method used industrially at present.

DETAILED DESCRIPTION

With the aim of obtaining strains that are overproducers of β-carotene, in the first place a mutagenic method was developed for the (+) and (−) strains of *B. trispora* with the mutagenic agents ethylmethane sulphonate (EMS) and N-methyl-N'-nitro-N -nitrosoguanidine (NTG). The suspensions of spores for mutation were obtained from slants with YpSs medium. The spores were resuspended by adding 10 ml of a solution of Triton X-100 at 0.1% to each slant. The mycelium residues were removed by filtration through a nylon filter with a pore size of 20 μm. The concentration of spores in the suspension was about $10^6$ spores/ml. The method of mutation with EMS consisted of incubating $10^6$ spores/ml in a 3% EMS solution in 0.1 M sodium phosphate buffer pH 7.0 at room temperature for 60 minutes, achieving mortality rates of around 99%. The mutated spores were washed three times with 0.1% Triton X-100 and centrifuged at 3000 rpm at 15° C. for 2 minutes. The method of mutation with NTG consisted of incubating $10^6$ spores/ml in a solution that contained 250 μg/ml of NTG and 0.1 M sodium citrate buffer pH 5.0 at room temperature for 30 minutes, achieving mortality rates of around 95%. The mutated spores were washed three times with 0.1% Triton X-100 and centrifuged at 3000 rpm at 15° C. for 2 minutes. Petri dishes containing Sutter IV solid medium supplemented with 0.1% Triton X-100 were seeded with the mutated spores and incubated at 25° C. for 4 days to obtain isolated colonies.

The strategies employed for selecting *B. trispora* (−) strains that are overproducers of β-carotene were as follows: (i) use of the cell selection technique based on fluorescence (FACS, fluorescent activated cell sorting), (ii) the lower yield of γ-carotene and other carotenoids and (iii) the color intensity of the colony. For selecting β-carotene-producing mutants using FACS, the mutated spores were grown on PDA medium, were washed with 0.1% Triton X-100 and were analyzed in a flow cytometer combined with a cell sorter and separator ("FACSort", Fluorescent Activated Cell Sorting). Using this technique, it is possible to select the subpopulation of mutants with the highest levels of autofluorescence. Although β-carotene is not actually a fluorescent molecule, when it is excited with an argon laser at 488 nm it emits fluorescent radiation that is detected at a wavelength above 600 nm. In this way, the autofluorescence detected is proportional to the content of β-carotene in the spore.

The selected spores were seeded on PDA medium (Difco) and were incubated at 25° C., observing that the mutants that are overproducers of β-carotene became a deep orange in color. Selection of β-carotene-producing mutants as a function of their lower yield of γ-carotene and other carotenoids was effected in the following way: the subpopulation of mutants with higher level of autofluorescence isolated by means of FACSort was fermented in liquid medium with the aim of determining the yields of β-carotene in mixed culture. Once fermentation had ended, β-carotene and other carotenoids were quantified by HPLC. In this way, mutants were selected that exhibited (i) a higher yield of β-carotene and (ii) a lower yield of γ-carotene and other carotenoids. Applying both methods with the VKPM F-744 (−) strain, we selected the strains CMA1 (−), CMA2 (−), CMA3 (−) and CMA4 (−) (Scheme 2).

Scheme 2. Phylogeny of the strains of *B. trispora* (−) obtained from *B. trispora* VKPM F-208 (−) using methods of mutation and selection. UV ultraviolet, SN natural selection, NTG N-methyl-N'-nitro-N-nitrosoguanidine, EMS ethylmethane sulphonate, FACS fluorescent activated cell sorting.

The following system of symbols was used for designating the strains selected: CM=carotene minus (−), CP=carotene plus (+). The relation between parent generations follows alphabetical order: A is the parent of B, B is the parent of C, etc. The number given after the letters corresponds to the number of the mutant. For example, the designation CMA1 (−) signifies that it is a carotene-producing strain (C), minus (M), parent of CMB and mutant number 1. In the same way, CMA1 (−), CMA2 (−), CMA3 (−) and CMA4 (−) correspond to mutants 1, 2, 3 and 4 of one and the same generation.

Selection of β-carotene-producing mutants as a function of the color intensity of the colony was carried out in the following way: the mutated spores of the CMA1 (−) strain were seeded on dishes of YEPDA solid medium and, once grown, those colonies that had a deeper yellowish-orange color than the CMA1 (−) parent strain were selected. In this way, 2 colonies with a deep yellowish-orange color were isolated, designated CMB1 (−) and CMB2 (−).

Selection of β-carotene-overproducing mutants of *B. trispora* (+) was effected by growing mutated spores on Petri dishes containing Sutter IV solid medium. Next, a portion from each of the colonies was transferred to a dish of PDA on which *B. trispora* (−) had been seeded previously. The yield of β-carotene on solid medium was estimated as a function of the color intensity in the zone of intersection of the colony of the (+) strain with that of the (−) strain. In this way, the strain *B. trispora* CPA1 (+) was selected (Scheme 3), which gave rise to a higher yield of β-carotene in mixed solid cultures with a series of (−) strains. The yield of the *B. trispora* CPA1 (+) strain was then analyzed in mixed culture on liquid medium.

Scheme 3. Phylogeny of the strains of *B. trispora* (+) obtained from *B. trispora* VKPM F-117 (+) using methods of mutation and selection. UV ultraviolet, SN natural selection, NTG N-methyl-N'-nitro-N-nitrosoguanidine, EMS ethylmethane-sulphonate.

The (+) and (−) strains of *B. trispora* selected on solid medium were fermented in a flask with the aim of determining the yield of β-carotene in liquid medium and mixed culture. For this, separate flasks of inoculum of the (+) and (−) strains were grown and then a mixed fermentation of the two strains was carried out in the flask. Once fermentation had ended (around 6 days), the mycelium of *B. trispora* was lysed by vortex agitation, the β-carotene was extracted with organic solvents (e.g. acetone) and its concentration and purity were determined by HPLC. The yields obtained varied between 6.0 and 7.0 g/l.

The selected strains were cultivated in pilot-plant fermenters for the purpose of determining the yield of β-carotene. For this, they were grown separately in flasks, transferred separately to intermediate growing tanks and finally they were fermented together. The fermentation was incubated for 100-140 hours. The mean yields of β-carotene obtained in a series of different fermentations were 7.2 g/l for the CPA1 (+)/CMA3 (−) strains and 6.8 g/l for the CPA1 (+)/CMB2 (−) strains. When, in the fermentation of the CPA1 (+)/CMA3 (−) strains, the age of the inocula was reduced from 48 to 46 hours, it was found that its yield had increased to 7.7 g/l. Similarly, when in the fermentation of the CPA1 (+)/CMB2 (−) strains the age of the inocula was reduced from 48 to 46 hours, it was found that its yield had increased to 7.1 g/l. Next, we succeeded in increasing the yield of β-carotene from the CPA1 (+)/CMA3 (−) strains by establishing an optimum program of addition of β-ionone. In this way, yields were attained in the range of 8.7 g/l. Finally, a fermentation system with oxygen injection was developed, and this made it possible (i) to increase the yield of β-carotene up to at least 9 g/l in fermentations of the CPA1 (+)/CMA3 (−) strains and (ii) to reduce the accumulation of γ-carotene and other carotenoids.

Deposit of Microorganisms in Accordance with the Treaty of Budapest

The strains of *Blakeslea trispora* have been deposited, in accordance with the provisions of the Treaty of Budapest, in the Russian National Collection of Industrial Microorganisms (VKPM), GNII Genetika, Dorozhny Proezd 1, Moscow 113545 (Russia), with the following numbers and dates: VKPM F-117 on Dec. 21, 1979, VKPM F-208 on Dec. 20, 1979, VKPM F-551 on Nov. 19, 1992, VKPM F-674 on Nov. 19, 1992, VKPM F-726 on Jan. 21, 1997, VKPM F-727 on Jan. 21, 1997, VKPM F-736 on Oct. 7, 1997, VKPM F-741 on Jan. 28, 1998, VKPM F-744 on Jan. 28, 1998 and VKPM F-816 on Dec. 13, 2000.

The following examples describe the present invention in detail and without limitation.

EXAMPLE 1

Strategies for Mutation of the (+) and (−) Strains of *B. Trispora*

Firstly a mutagenic method was developed for the (+) and (−) strains of *B. trispora*, for which the following were analyzed: (i) various types of mutagenic agents, (ii) concentration of the mutagen, (iii) concentration of spores, (iv) incubation pH, and (v) treatment time. In this way, ethylmethane sulphonate (EMS) and N-methyl-N'-nitro-N-nitrosoguanidine (NTG) were selected as mutagenic agents.

The suspensions of spores to be mutated were obtained from slants with YpSs medium, which has the following composition: yeast extract 4 g/l, soluble starch 15 g/l, $K_2HPO_4$ 1 g/l, $MgSO_4 \cdot 7H_2O$ 0.5 g/l and agar 15 g/l, at a final pH of 5.8. The spores were resuspended by adding 10 ml of a 0.1% solution of Triton X-100 to each slant. The mycelium residues were removed by filtration through a nylon filter with pore size of 20 μm. The concentration of spores in the suspension was about $10^6$ spores/ml.

The method of mutation with EMS consisted of incubating $10^6$ spores/ml in a solution of EMS at 3% in 0.1 M sodium phosphate buffer pH 7.0 at room temperature for 60 minutes, achieving mortality rates of around 99%. The mutated spores were washed three times with 0.1% Triton X-100, centrifuging at 15° C. and 3000 rpm for 2 minutes.

The method of mutation with NTG consisted of incubating $10^6$ spores/ml in a solution that contained 250 μg/ml of NTG and 0.1 M sodium citrate buffer pH 5.0 at room temperature for 30 minutes, achieving mortality rates of around 95%. The mutated spores were washed three times with 0.1% Triton X-100, centrifuging at 15° C. and 3000 rpm for 2 minutes.

The mutated spores were used for seeding Petri dishes that contained Sutter IV solid medium supplemented with 0.1% Triton X-100. The composition per liter of the Sutter IV medium is as follows: 40 g glucose, 4 g L-asparagine, 10 g $KH_2PO_4$, 40 ml of solution of trace elements 50x, and 30 g of agar. The solution of trace elements 50x is made up of: 25 g/l of $MgSO_4.7H_2O$, 1.82 g/l of $CaCl_2.2H_2O$, 0.05 g/l of thiamine, 0.1 g/l of citric acid, 0.075 g/l of $Fe(NO_3)_3.9H_2O$, 0.05 g/l of $ZnSO_4.7H_2O$, 0.17 g/l of $MnSO_4.H_2O$, 0.025 g/l of $CuSO_4.5H_2O$ and 0.025 g/l of $NaMoO_4.2H_2O$. The seeded dishes were incubated at 25° C. for 4 days to obtain isolated colonies.

EXAMPLE 2

Strategies for Selecting Mutants of *B. Trispora* (−) that are Overproducers of β-Carotene This example describes strategies for selecting β-carotene-overproducing strains of *B. trispora* (−) based on (i) use of the cell selection technique based on fluorescence (FACS, fluorescent activated cell sorting), (ii) lower yield of γ-carotene and other carotenoids and (iii) the color intensity of the colony. The phylogeny of the *B. trispora* (−) strains used in the present invention is shown in Scheme 2.

Figure 1:
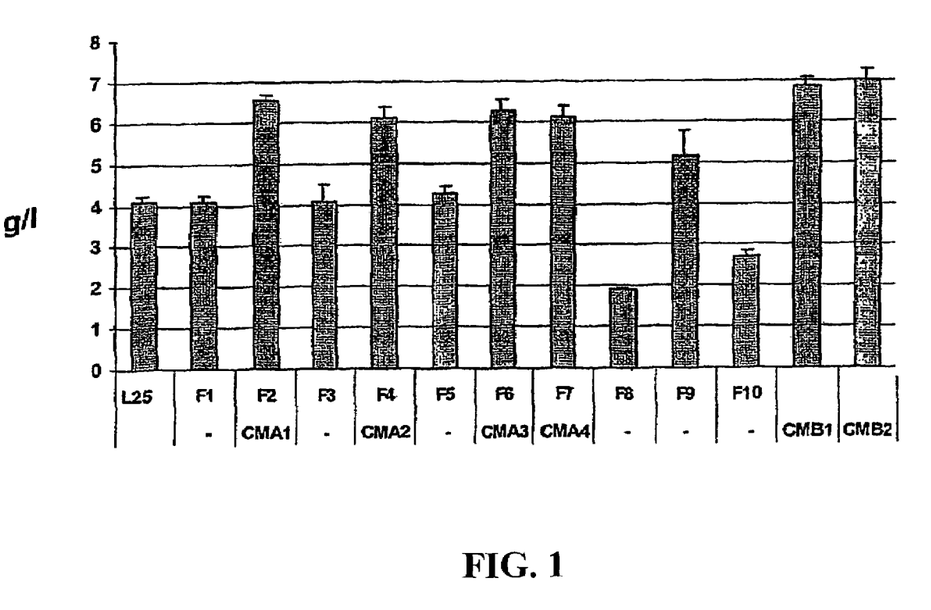
FIG. 1. Production of β-carotene by mixed flask fermentation of the CPA1 (+) strain of *B. trispora* with a series of (−) strains of *B. trispora*. Ordinate: g/l: Abscissa: $F_1$, $F_2$, etc., mutants selected with the FACsort system, from which CMA1, CMA2, CMA3 and CMA4 were chosen after flask fermentation (example 2). L25 corresponds to VKPM F-744 (−).

Selection of β-carotene-producing mutants by means of FACS was carried out starting from spores mutated with EMS as described in example 1. The mutated spores were seeded on PDA solid medium and were incubated at 25° C. for 7 days. At the end of this time, the spores were collected by centrifugation and were washed twice with a 0.1% solution of Triton X-100. Each dish was suspended in a final volume of 1 ml. The mutant spores of *B. trispora* were analyzed by flow cytometry in a FACSort instrument (Becton Dickinson). Excitation was effected with an argon laser at 488 nm, evaluating the following parameters: forward scattering (FSC), side scattering (SSC) and fluorescence emission starting from 600 nm (by using the FL3 detector). Mutants that are overproducers of β-carotene were selected by purification of the subpopulation of spores that possessed the highest levels of autofluorescence in the FL3 detector. The spores isolated in this way were seeded on PDA medium with the aim of obtaining isolated colonies. The yield of each of the colonies was analyzed by flask fermentation in mixed culture with the *B. trispora* CPA1 (+) strain as described in example 4. The results obtained with 10 mutant colonies were as follows: 5 colonies (50%) displayed a significant increase in β-carotene yield relative to the *B. trispora* VKPM F-744 (−) parent strain, 30% of the colonies displayed yields similar to the parent strain and the remaining 20% produced smaller quantities than the parent strain (FIG. 1). Of the 5 mutants that had an increased yield of β-carotene (CMA1 (−), CMA2 (−), CMA3 (−), CMA4 (−) and F9 (−)), only one of them (F9 (−)) had higher levels of γ-carotene and other carotenoids, and was therefore discarded. The strain with the highest purity and yield of β-carotene was CMA1 (−), and it was therefore selected as the parent strain of the next cycle of mutation (Scheme 2).

Selection of mutants that are overproducers of β-carotene as a function of the color intensity of the colony was carried out as follows: the CMA1 (−) strain was submitted to mutagenesis as described in example 1. The mutated spores were seeded on dishes of YEPDA solid medium (bactopeptone 20 g/l, yeast extract 10 g/l, glucose 20 g/l and agar 20 g/l, at a final pH of 6.0), incubated at 25° C. for 24 hours and then at 20° C. for 48-72 hours. Finally, those colonies were selected that possessed a deeper yellowish-orange color than the CMA1 (−) parent strain. In this way 2 colonies with deep orange color were isolated, designated CMB1 (−) and CMB2 (−), which might be overproducers of β-carotene. The yield level of the *B. trispora* strains CMA1 (−), CMA2 (−), CMA3 (−), CMA4 (−), CMB1 (−) and CMB2 (−) was then analyzed in mixed culture with the CPA1 (+) strain on liquid medium as described in examples 4, 5, 6 and 7. Scheme 2 shows the phylogeny of the strains of *B. trispora* (−) used in the present invention.

EXAMPLE 3

Strategies for Selecting Mutants of *B. Trispora* (+) that are Overproducers of β-Carotene Selection of β-carotene-overproducing mutants of *B. trispora* (+) was effected using mutated spores as described in example 1. These spores were seeded on Petri dishes that contained Sutter IV solid medium and were incubated at 25° C. for 7 days to obtain isolated colonies. Next, a portion from each of the colonies was transferred to a dish of PDA medium on which *B. trispora* (−) had been seeded previously. The distance between the seeding points of the (+) and (−) strains must be approximately 2 cm. The yield of β-carotene in solid medium is estimated from the intensity of coloration in the zone of intersection of the colony of the (+) strain with that of the (−) strain. In this way the *B. trispora* strain CPA1 (+) was selected, and this gave rise to a higher yield of β-carotene in mixed solid cultures with a series of (−) strains. The yield of the *B. trispora* strain CPA1 (+) was then analyzed in mixed culture in a liquid medium as described in examples 4, 5, 6 and 7. Scheme 3 shows the phylogeny of the *B. trispora* (+) strains used in the present invention.

EXAMPLE 4

Method of Production of β-Carotene in a Flask by Mixed Culture of the (+) and (−) Strains of *B. Trispora*

The (+) and (−) strains of *B. trispora* selected as described in examples 1, 2 and 3 were fermented in a flask with the aim of determining the level of production of β-carotene in a liquid medium and mixed culture. For this, an inoculum medium was prepared with the following composition per liter: 23 g of soya flour, 47 g of maize flour, 0.5 g of $KH_2PO_4$ and 0.002 g of thiamine hydrochloride. The pH was adjusted to 6.3. The (+) strain was seeded in 500-ml flasks containing 67 ml of medium at the rate of $10^3$ spores per ml. The (−) strain was seeded in 500-ml flasks containing 100 ml of medium at a rate of $10^4$ spores per ml. Both types of inoculum were incubated at 25° C. and 250 rpm for 44 hours.

The fermentation medium has the following composition per liter: 44 g of soya flour, 19 g of maize flour, 10 g of orange flour, 0.5 g of $KH_2PO_4$, 0.28 g of isoniazid, 0.002 g of thiamine hydrochloride, 10 g of lecithin and 100 g of vegetable oil. The pH was adjusted to 6.3. The medium was distributed in 250-ml Erlenmeyer flasks, at the rate of 20 ml per flask. The flasks containing the fermentation medium were inoculated with 10% of a mixture of the (+) and (−) strains in the ratio 1/10. The flasks were incubated at 25° C. and 250 rpm and, at 48 hours, β-ionone was added at a rate of 1 ml per liter of culture medium. At the end of fermentation (6 days), a mixture of fermentation medium and methylene chloride/methanol (1/1) was prepared. Mixing with the solvent caused lysis of the mycelium of B. trispora, thus releasing the intracellular β-carotene. The β-carotene was extracted in the organic phase and was then diluted in acetone. The concentration and purity of the β-carotene were determined using reversed-phase HPLC.

The yields obtained in mixed fermentations of the CPA1 (+) strains with the CMA1 (−), CMA2 (−), CMA3 (−), CMA4 (−), CMB1 (−) and CMB2 (−) strains varied between 6.0 and 7.0 g/l (FIG. 1).

EXAMPLE 5

Method of Production of β-carotene by Mixed Cultivation of the (+) and (−) Strains of B. Trispora in a Fermenter The B. trispora strains CMA1 (−), CMA2 (−), CMA3 (−), CMB1 (−) and CMB2 (−), selected as described in examples 2, 3 and 4, were cultivated in pilot-stage fermenters together with the CPA1 (+) strain for the purpose of determining the yield of β-carotene. For this, an inoculum medium was prepared with the following composition per liter: 23 g of soya flour, 47 g of maize flour, 0.5 g of $KH_2PO_4$, 0.002 g of thiamine hydrochloride. The pH was adjusted to 6.3. The (+) and (−) strains were seeded separately in 2000-ml flasks containing 500 ml of medium and were incubated at 25° C. and 250 rpm for 44-48 hours.

Each of the strains was transferred at 0.1% to a vegetative growing tank containing a culture medium with the following composition per liter: 29 g of Pharmamedia, 47 g of maize flour, 0.5 g of $KH_2PO_4$, 0.002 g of thiamine hydrochloride and 1 g of antifoaming agent, and its pH was adjusted to 6.0. The (+) strain was incubated at 25-27° C. with aeration of 0.66 v/v/m (volume/volume/minute) and the (−) strain at 27-29° C. with aeration of 1.5 v/v/m. These differences in the incubation conditions give rise to differences in growth of the two strains, so that at the time of mixing in the fermenter the physiological state is suitable for achieving a maximum yield.

After incubating for 46 h, the (+) and (−) strains were mixed in the ratio 1/10, and 10% of the mixture was used for seeding the fermentation medium, which had the following composition per liter: 50 g of soya flour, 25 g of maize flour, 15 g of orange flour, 0.5 g of $KH_2PO_4$, 0.28 g of isoniazid, 0.002 g of thiamine hydrochloride, 10 g of soya lecithin, 80 g of vegetable oil and 0.175 g of antifoaming agent, with initial pH adjusted to 5.9. The fermentation was incubated for 120-140 hours at a temperature of 25-28° C. with stirring varying between 150 and 250 rpm and aeration of 1-1.5 v/v/m. The pH was controlled with ammonia or phosphoric acid. Between the 40th and 50th hours of fermentation, 10 g of a 10% solution of β-ionone in vegetable oil was added per liter of fermentation medium. Similarly, between the 70th and 80th hours of fermentation, 10 g of a 10% solution of ethoxyquin in vegetable oil was added per liter of fermentation medium.

Figure 2:
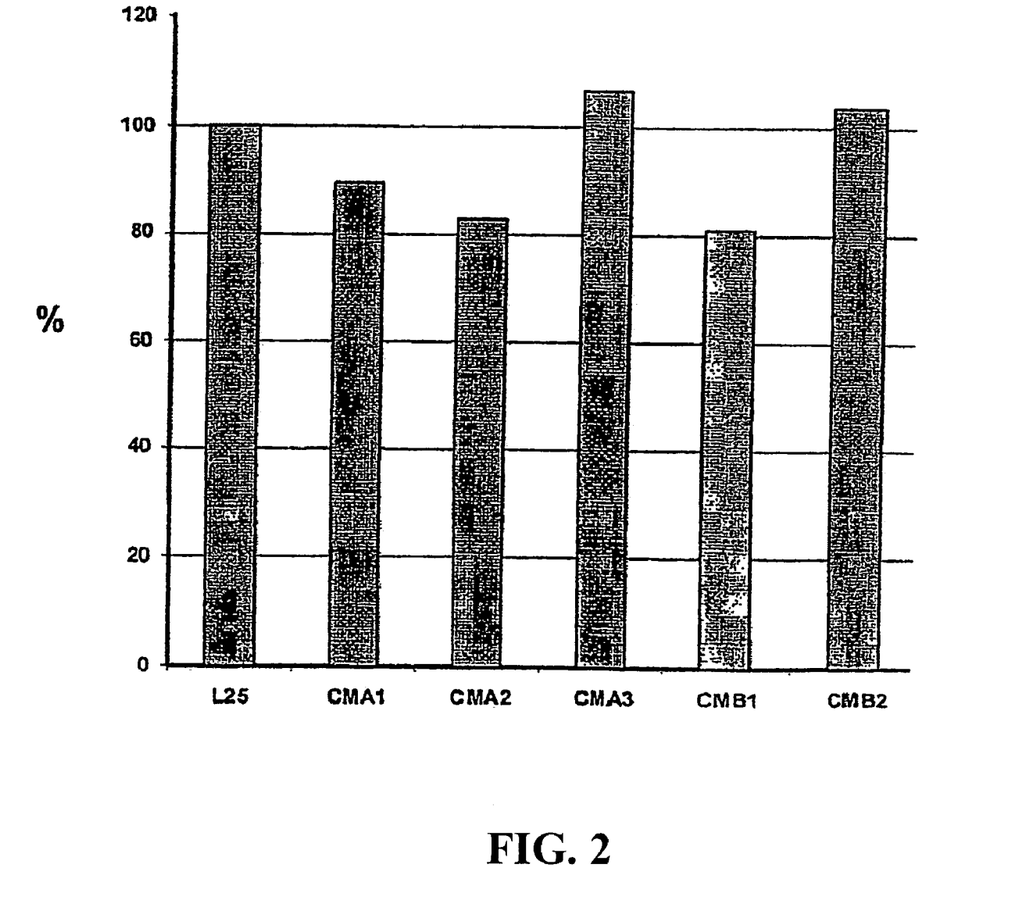
FIG. 2. Production of β-carotene by mixed fermentation of the CPA1 (+) strain of *B. trispora* with a series of (−) strains of *B. trispora* in a fermenter. Ordinate: % relative to the yield of L25 (−) L25 (−) corresponds to VKPM F-744 (−).

The concentration and purity of the β-carotene at the end of fermentation were evaluated as described in example 4. The results obtained are shown in FIG. 2. The average yield of β-carotene obtained in a series of different fermentations of the CPA1 (+) and CMA3 (−) strains was 7.2 g/l in the fermenter that proceeded from inocula incubated for 48 hours and 7.7 g/l when the inocula had been incubated for 46 hours. The yield of the CPA1 (+) and CMB2 (−) strains was 6.8 g/l in the fermenter that proceeded from inocula incubated for 48 hours and 7.1 g/l when the inocula had been incubated for 46 hours. This means that a decrease of 2 hours in the incubation time of the inoculum increased the yield of β-carotene by around 5-7%. This example clearly demonstrates how the yield of β-carotene is influenced by (i) the incubation time and (ii) the growing conditions established for each of the two strains.

EXAMPLE 6

Method of Production of β-Carotene by Mixed Cultivation of the CPA1 (+) and CMA3 (−) Strains of B. Trispora in a Fermenter Using a Specific Program of Addition of β-ionone The CPA1 (+) and CMA3 (−) strains, selected as described in examples 2, 3 and 4, were cultivated in a pilot-stage fermenter with the aim of determining the yield of β-carotene. The fermentation conditions (inocula, vegetative growing tanks and fermenter) were as described in example 5, but with a different program of addition of β-ionone.

The program of addition of β-ionone established in example 5 consisted of supplying, between the 40th and 50th hours of fermentation, 10 g of a 10% solution of β-ionone in vegetable oil per liter of fermentation medium. In this case a new series of programs of addition was analyzed, obtaining the following improved results: 10 g of a 10% solution of β-ionone in vegetable oil per liter of fermentation medium between the 40th and 50th hours of fermentation, a further 10 g per liter between the 60 and 70th hours of fermentation and another 5 g per liter between the 100th and 105th hours of fermentation.

The concentration and purity of the β-carotene at the end of fermentation were evaluated as described in example 4. The average yield of β-carotene obtained in a series of different fermentations of the CPA1 (+) and CMA3 (−) strains was 7.2 g/l using the program of addition of β-ionone described in example 5 and 8.7 g/l with the improved program described in the present example. These results confirm that there is a close relation between the program of addition of β-ionone and the yield of β-carotene.

EXAMPLE 7

Method of Production of β-Carotene by Mixed Cultivation of the (+) and (−) Strains of B. Trispora in a Fermenter Using Oxygen Injection The strains of B. trispora CPA1 (+) and VKPM F-744 (−), selected as described in examples 2 and 3, were cultivated in a pilot-stage fermenter with the aim of determining the yield of β-carotene. The fermentation conditions (inocula, intermediate growing tanks and fermenter) were as described in example 5, but increasing the quantity of oxygen dissolved in the fermentation medium by injection of oxygen.

Standard fermentation (without extra addition of oxygen) was carried out with a pattern of stirring varying between 150 and 250 rpm and aeration of 1-1.5 v/v/m. In the case of fermentation with oxygen injection, the same conditions were employed except that the air entering the fermenter had been enriched with oxygen by connecting to bottles of pure oxygen. In this way the oxygen content of the air was increased from 21% to 24.5%. Oxygen supplementation was carried out between the 40th and 70th hours of fermentation. The average concentration of oxygen dissolved in the fermentation medium in the conditions with oxygen supplementation reached values of 49%, whereas this value was 34% without addition of oxygen.

Figure 3:
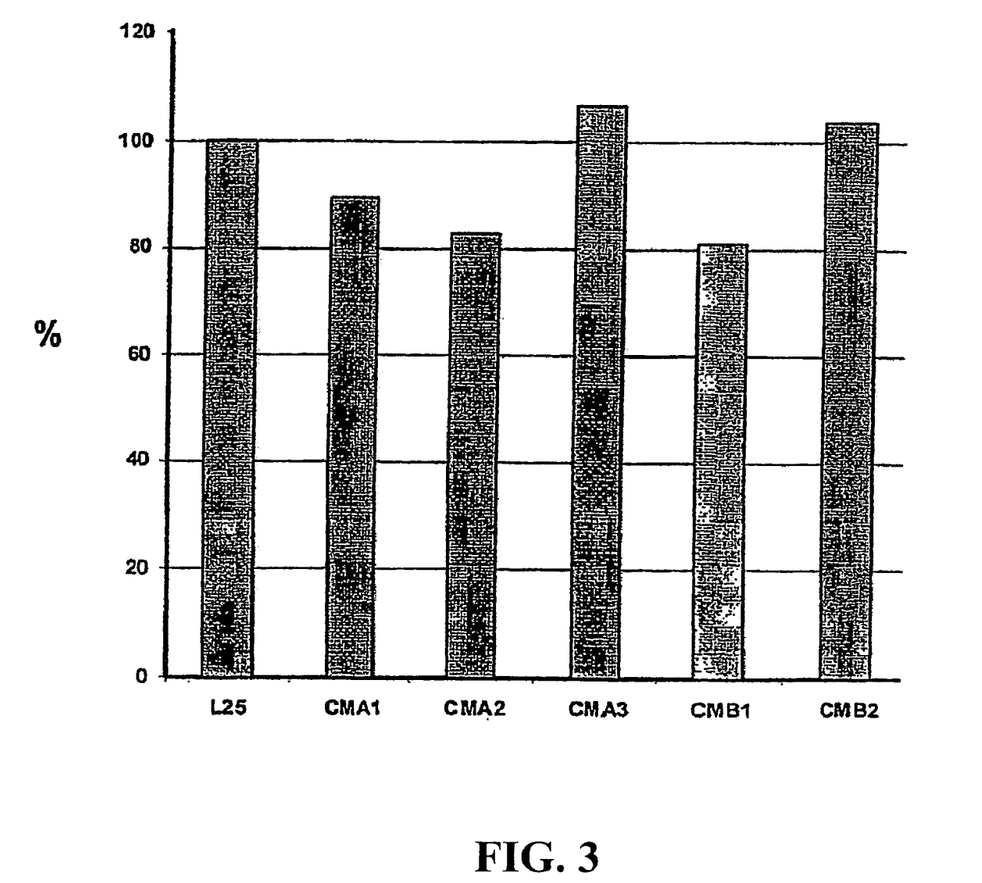
FIG. 3. Production of β-carotene by mixed fermentation of the strains CPA1 (+)/L25 (−) and CPA1 (+)/CMA3 (−) in a fermenter without direct injection of oxygen (standard) or using direct injection of oxygen. Ordinate: g/l. L25 (−) corresponds to VKPM F-744 (−).

The concentration and purity of the β-carotene at the end of fermentation were evaluated as described in example 4. The average yield of β-carotene obtained in a series of different fermentations of the CPA1 (+) and VKPM F-744 (−) strains was 6.7 g/l without addition of oxygen and 7.1 g/l when oxygen was injected. This demonstrates that it is possible to increase the yield of β-carotene by supplying extra oxygen at those moments during fermentation when the concentration of oxygen dissolved in the fermentation medium is at its minimum. Applying this technology to the fermentation conditions established in example 6 for the CPA1 (+) and CMA3 (−) strains, yields greater than 9 g/l were obtained (FIG. 3).

In addition, oxygen enrichment of the air entering the fermenter gave rise to a decrease in the yield of other unwanted carotenoids such as γ-carotene and β-zeacarotene. The average yield of γ-carotene (as a percentage relative to β-carotene) in the series of experiments previously described was 1.8% without oxygen injection and 1.2% with injection of oxygen. Moreover, the values for β-zeacarotene were 1.0% without oxygen injection and only 0.5% when oxygen was injected. It is concluded on the basis of these results that there is a close relation between oxygenation of the culture and (i) the increase in β-carotene yield and (ii) the decrease in levels of γ-carotene and β-zeacarotene.

The invention claimed is:

1. In a method of production of β-carotene by fermentation with mixed cultures of (+) and (−) strains of *B. trispora*, the improvement comprising fermenting the cultures in a plurality of vegetative growth stages, including an initial stage wherein spores of each of the (+) and (−) strains that have been seeded in respective inoculum media are incubated to form respective primary cultures of the (+) and (−) strains of *B. trispora*, a cultivation stage wherein the primary cultures of the (+) and (−) strains are cultivated, and a fermentation stage wherein the cultivated primary cultures are mixed and fermented in a fermentation medium, wherein β-ionone and oxygen are added to the fermentation medium in the fermentation stage, the β-ionone being added in an amount that improves the yield of β-carotene as compared with the yield if the β-ionone were not added, the oxygen being added in an amount that decreases a yield of caratenoids other than β-carotene compared with the yield of the other carotenoids if the oxygen were not added, each of the plurality of vegetative growth stages having a duration that is controlled such that the method yields a minimum of 6 g/l of β-carotene in 5-6 days.

2. A method according to claim 1, wherein the inocula are incubated in the initial stage for a period of between 42 to 50 hours.

3. A method according to claim 2, wherein the inocula are incubated in the initial stage for a period of about 46 hours.

4. A method according to claim 1, wherein the primary cultures of the (+) and (−) strains are cultivated in the cultivation stage for a period of between 35 and 55 hours.

5. A method according to claim 4, wherein the primary cultures of the (+) and (−) strains are cultivated in the cultivation stage for a period of between 44 and 48 hours.

6. A method according to claim 1, wherein β-ionone is added in cycles during the fermentation stage from the $40^{th}$ hour to the $105^{th}$ hour, said cycles comprising at least 3 cycles.

7. A method according to claim 6, wherein the at least 3 cycles are between the $40^{th}$ and $50^{th}$ hours, between the $60^{th}$ and $70^{th}$ hours and between the $100^{th}$ and $105^{th}$ hours.

8. A method according to claim 6, wherein at least 10 g of a 10% solution of β-ionone in vegetable oil per liter of the fermentation medium is added in each of 2 of the at least 3 cycles, and at least 5 g of the solution per liter of the fermentation medium is added in a third of the at least 3 cycles.

9. A method according to claim 1, wherein oxygen is added from the start until the end of the fermentation stage.

10. A method according to claim 1, wherein oxygen is added between the $40^{th}$ and $70^{th}$ hours of the fermentation stage.

11. A method according to claim 1, wherein oxygen is added during the fermentation stage such that average values of oxygen dissolved in the fermentation medium are maintained between 35 and 60%.

12. A method according to claim 11, wherein the average value of oxygen dissolved in the fermentation medium is about 50%.

13. A method according to claim 1, wherein:
   (a) inocula of the (+) strain of *B. trispora* are seeded in a range of 800-1000 spores/ml.
   (b) inocula of the (−) strain of *B. trispora* are seeded in a range of 10 000-60 000 spores/ml,
   (c) the inocula of the (+) and (−) strains of *B. trispora* are cultivated for about 46 hours at 25° C.,
   (d) primary culture phases of the (+) strain of *B. trispora* are seeded with about 0.1% (v/v) of the inoculum phase,
   (e) primary culture phases of the (−) strain of *B. trispora* are seeded with about 0.1% (v/v) of the inoculum phase,
   (f) the primary phases of the (+) strain of *B. trispora* are cultivated for about 44-48 hours at 26° C.,
   (g) the primary phases of the (−) strain of *B. trispora* are cultivated for about 44-48 hours at 28° C.,
   (h) the primary phases of the (+) and (−) strains of *B. trispora* are mixed in an approximate ratio of 1 (+)/10 (−) (v/v) to form a mixture,
   (i) each fermenter is seeded with 10% (v/v) of the mixture of the (+) and (−) strains of *B. trispora* described in paragraph h,
   (j) the mixture is incubated for 5-6 days at 26° C.

14. A method according to claim 1, wherein the method yields β-carotene and mycelium with at least 100 mg of β-carotene being produced per gram dry weight of mycelium.

15. A method according to claim 1, wherein the method also produces γ-carotene, wherein γ-carotene is produced at levels that are below 1.2% those of the β-carotene produced.

16. A method according to claim 1, wherein the method also produces β-zeacarotene, wherein β-zeacarotene is produced at levels that are below 0.5% those of the β-carotene produced.

* * * * *